(12) United States Patent
Cronin

(10) Patent No.: US 6,425,759 B1
(45) Date of Patent: Jul. 30, 2002

(54) DENTAL CAST TRAY ASSEMBLY

(76) Inventor: Richard J. Cronin, 45 Cypress St., Medfield, MA (US) 02052

(*) Notice: Subject to any disclaimer, the term of this patent is extended or adjusted under 35 U.S.C. 154(b) by 0 days.

(21) Appl. No.: 09/713,126

(22) Filed: Nov. 15, 2000

(51) Int. Cl.[7] .............................. A61C 9/00
(52) U.S. Cl. ....................................... 433/34
(58) Field of Search .................. 433/34, 74, 60, 433/45; 249/54

(56) References Cited

U.S. PATENT DOCUMENTS

| | | | |
|---|---|---|---|
| 4,035,916 A | 7/1977 | Eveland | |
| 4,139,943 A | 2/1979 | Dragan | |
| 4,265,619 A | 5/1981 | Lucki et al. | 433/54 |
| 4,363,625 A | 12/1982 | der Avanessian | 433/74 |
| 4,508,506 A | 4/1985 | Jackson | 433/74 |
| 4,538,987 A * | 9/1985 | Weissman | 433/60 |
| 4,608,016 A | 8/1986 | Zeiser | 433/74 |
| 4,767,330 A | 8/1988 | Burger | 433/213 |
| 4,898,359 A | 2/1990 | Gopon | 249/54 |
| 4,957,435 A * | 9/1990 | Jinoian et al. | 433/34 |
| 5,352,117 A | 10/1994 | Silva | 433/60 |
| 5,393,227 A | 2/1995 | Nooning | 433/74 |
| 5,506,095 A | 4/1996 | Callne | 433/34 |
| 5,913,681 A * | 6/1999 | Cho | 433/60 |
| 6,099,305 A * | 8/2000 | Browne et al. | 433/34 |
| 6,106,284 A | 8/2000 | Cronin | 433/34 |

\* cited by examiner

*Primary Examiner*—John J. Wilson
*Assistant Examiner*—Melba Bumgarner
(74) *Attorney, Agent, or Firm*—Kriegsman & Kriegsman

(57) ABSTRACT

A dental cast tray assembly used to form a dental cast model comprises a base and a tray removably mounted on the base. The base includes a top surface, a flat bottom surface and a plurality of cylindrically-shaped projections formed on the top surface. The tray includes a bottom surface and a top surface. The bottom surface of the tray is generally flat and includes a plurality of openings, each opening being sized and shaped to receive an associated projection therewithin when the tray is mounted on the base. The top surface of the tray is recessed to form a support surface and a sidewall protruding up from the support surface, the support surface and the sidewall together defining an enclosed reservoir for holding the dental cast model. A plurality of spaced apart retention walls are formed on the support surface of the tray for retaining the dental cast model.

20 Claims, 6 Drawing Sheets

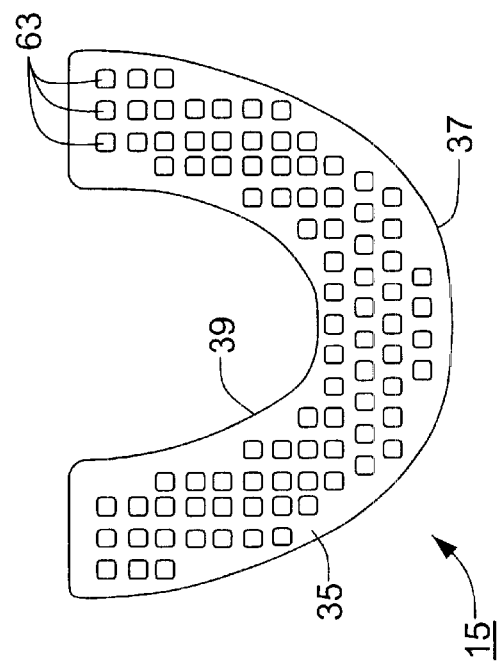
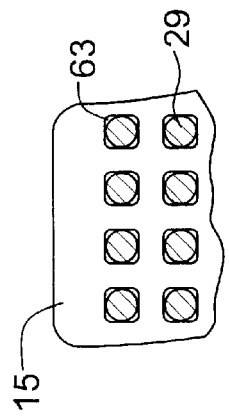
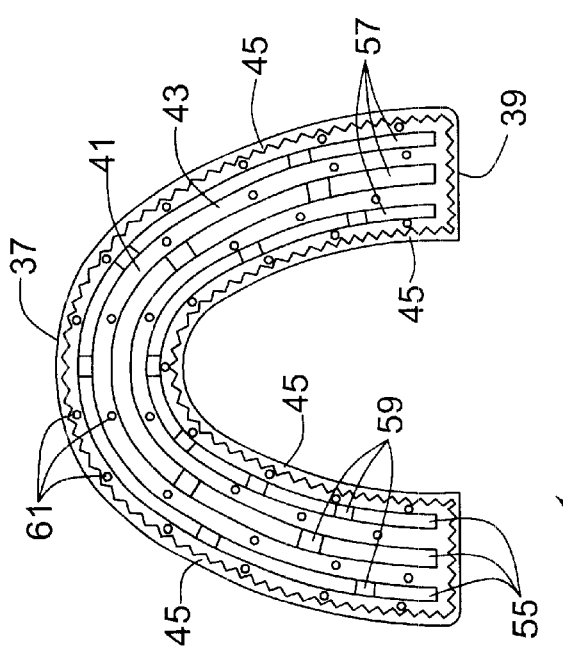
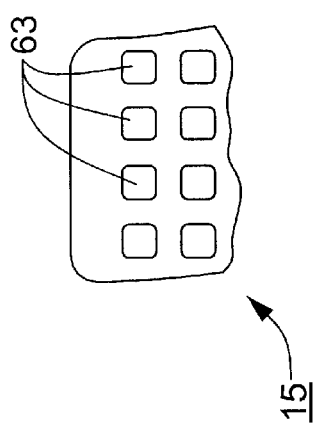
FIG. 10
FIG. 12
FIG. 11
FIG. 7

DENTAL CAST TRAY ASSEMBLY

BACKGROUND OF THE INVENTION

The present invention relates generally to the dental industry and, more particularly, to dental tools which are used in the production of dental cast models.

In the dental industry, technicians commonly construct dental models. A dental model of the entire mouth of a patient typically comprises an upper jaw model and a lower jaw model which are affixed to one another by an articulator. An articulator is a device comprising upper and lower mounting platforms which are connected to the upper and lower jaw model elements. The articulator enables for centric, lateral and protrusive movement of the upper jaw model relative to the lower jaw model in order to closely simulate the relationships and the actual movement, or bite, of the mouth of the patient.

Various types of devices and procedures have been used in the art for creating dental models.

One method for manufacturing dental models which is well known and commonly used in the art involves molding the dental model using a casting material. Specifically, one or more impression trays are filled with rubber based impression material. Each impression tray is then urged into the mouth of the patient so as to create a negative impression of the teeth of the patient into the rubber based impression material. If necessary, excess impression material is trimmed from the impression tray after the negative impression is formed.

After the negative impression has been formed, the impression tray is typically transported to a dental laboratory where the dental cast model is manufactured. Specifically, the negative impression created in the impression tray is filled with a soft casting material, such as dental stone, plaster or epoxy. The impression tray is then inverted and mounted upon a pre-formed mounting device, such as a dental cast tray or base. After the casting material has had an opportunity to harden, the impression tray is removed so that the casting material forms a positive dental impression on the mounting surface.

Molded dental models are often used to manufacture crowns, bridges, inlays, dentures and other dental prosthetics outside of the mouth of the patient. The construction of dental prosthetics typically necessitates the ability to remove one or more individual model teeth from its spatial physical relationship relative to the remainder of the dental cast model for the purpose of constructing accurate margins and contours. In the event that two or more individual units of bridgework are to be joined, it is necessary that the working model segments be accurately and repeatedly returned to their original relationships precisely as they existed prior to any cutting, separations or disassembly of the model.

In order to effectively remove an individual model segment from the remainder of the dental model, the entire jaw model is typically removed from the mounting device and positioned upon a flat cutting surface, such as a table. A cutting device, such as a saw, can then be used to separate the desired model teeth from the remainder of the dental model. After the technician has completed manufacture of the dental work, the dental model can be re-assembled onto the mounting device.

It should be noted that during the re-assembly of the dental cast model, it is essential that precise registration and desired alignment be maintained between the working model segments and the remainder of the molded dental cast model.

In U.S. Pat. No. 5,393,227 to W. H. Nooning, there is disclosed a dental impression handling tool consisting of two base structures shaped to approximate two opposite quadrants of a full dental arch, and two similarly-shaped inserts that snap fit into the base structures. Each base includes a wide, upward facing trough approximating the placement and curvature of teeth within a dental quadrant. The upper surface of each insert is attached to a positive dental mold by means of protrusions that extend from the top horizontal surface of the insert, the protrusions being encased within the mold material. Positive positional relationship is maintained between each base and its mating insert by the use of an interlocking and non-recurring geometric pattern that is carried by the internal vertical walls of the trough in the base, and by a matching geometric pattern that is carried by the outer vertical walls of two vertically downward extending ribs on the underside of the insert. A second deeper, narrow and centrally located trough is formed in each base. This second trough mates with a third center rib that protrudes from the bottom surface of each insert. The insert's center rib contains a retainer bead along both vertical side walls. This bead provides a snap-lock fit into a corresponding negative indentation formed along the vertical side walls of the center trough of in each base. The center rib in each insert contains cylindrical cavities which allow the insertion of standard dental dowels or suitable substitutes.

Dental impression handling tools of the type described above in Nooning have been found to be experience numerous drawbacks.

As a first drawback, dental impression handling tools of the type described above in Nooning are undesirable in that the base comprises an elongated slot into which debris, such as plaster, can collect. As a result, it has been found that the insert is often unable to secure a proper fit within the base structure, thereby precluding proper alignment, which is highly undesirable.

As a second drawback, dental impression handling tools of the type described in Nooning are undesirable in that the bottom surface of the each insert includes various sized ribs, thereby creating a bottom surface which is highly unstable. As a result, when the insert is placed upon a laboratory table in order to cut the desired model teeth from the remainder of the dental cast model, the non-flat and unstable nature of the bottom surface of each insert renders the cutting process extremely difficult, which is highly undesirable.

Accordingly, in U.S. Pat. No. 6,106,284 to R. J. Cronin et al., there is disclosed, in one embodiment, a dental cast tray assembly used to form a dental cast model which comprises a base and a tray removably mounted on the base. The base includes a top surface, a flat bottom surface, a front wall, a rear wall and a plurality of projections formed on its top surface in a non-recurring, random pattern. Each of the plurality of projections is generally cylindrically-shaped and includes a convex free end. The tray includes a top surface adapted to support the dental cast model, a flat bottom surface, a front wall, a rear wall, a retention bar formed on its top surface and a plurality of openings formed in its bottom surface in the same non-recurring, random pattern in which the plurality of projections are disposed on the base. Each of the plurality of openings is defined by four sidewalls and is generally hourglass shaped in lateral cross-section. Two of the four sidewalls which define each of the plurality of openings include an elongated rib. In use, the tray is mounted on the base such that the bottom surface of the tray abuts against the top surface of the base and so that the front wall of the tray is flush with the front wall of the base. With the tray mounted on the base, one projection in the base projects into an associated opening in the tray, the elongated ribs serving to retain each projection within its associated opening with limited retention.

Although highly effective in constructing a dental cast model, the dental cast tray assembly described in Cronin et al. suffers from a couple notable drawbacks.

As a first drawback, the dental cast tray assembly described in Cronin et al. is difficult to manufacture due to the T-shape of the retainer bar. Specifically, the undercuts of the T-shaped retainer bar are difficult to create using conventional molding processes, thereby increasing the overall cost to manufacture the dental cast tray assembly, which is undesirable.

As a second drawback, utilization of the dental cast tray assembly described in Cronin et al. often requires considerable clean-up. Specifically, in use, casting material is spread both within the negative impression of the impression tray and onto the top surface of the tray around the retention bar. However, it has been found that, before the casting material has had a chance to harden, some of the casting material often drips off of the top surface of the tray and onto the base and working table. As a result, the dental technician is often required to spend a considerable amount of time and energy to clean-up the excess casting material which accumulates on the base and the working surface, which is undesirable.

As a third drawback, the dental cast tray assembly described in Cronin et al. is often difficult to use. Specifically, in use, casting material is spread both within the negative impression of the impression tray and onto the top surface of the tray around the retention bar. However, it has been found that the application of the casting material around the entire retention bar is often difficult to achieve due to the undercuts of the T-shaped retention bar. As a result, if the casting material is not properly spread around the entire retaining bar, air gaps can form between the plaster and the tray, thereby weakening the strength of the retention of the dental cast model on the tray, which is undesirable.

SUMMARY OF THE INVENTION

It is an object of the present invention to provide a new and improved dental cast tray assembly which can be used to produce a dental cast model.

It is another object of the present invention to provide a dental cast tray assembly as described above which includes a tray on which the dental cast model is mounted.

It is yet another object of the present invention to provide a dental cast tray assembly as described above which allows for repeated removal and replacement of the tray onto a base with proper alignment.

It is still another object of the present invention to provide a dental cast tray assembly as described above which enables the dental cast model to be easily cut into working segments.

It is another object of the present invention to provide a dental cast tray assembly as described above wherein the tray is constructed to securely retain the dental cast model thereon.

It is still another object of the present invention to provide a dental cast tray assembly as described above which is inexpensive to manufacture, has a minimal number of parts, is limited in size and can be very easily used.

Accordingly, there is provided a dental cast tray assembly for forming a dental cast model, comprising a base, and a tray removably mounted on said base, said tray comprising a bottom surface and a top surface, the top surface being recessed so as to form an enclosed reservoir for holding the dental cast model.

Additional objects, as well as features and advantages, of the present invention will be set forth in part in the description which follows, and in part will be obvious from the description or may be learned by practice of the invention. In the description, reference is made to the accompanying drawings which form a part thereof and in which is shown by way of illustration various embodiments for practicing the invention. The embodiments will be described in sufficient detail to enable those skilled in the art to practice the invention, and it is to be understood that other embodiments may be utilized and that structural changes may be made without departing from the scope of the invention. The following detailed description is, therefore, not to be taken in a limiting sense, and the scope of the present invention is best defined by the appended claims.

BRIEF DESCRIPTION OF THE DRAWINGS

The accompanying drawings, which are hereby incorporated into and constitute a part of this specification, illustrate various embodiments of the present invention and, together with the description, serve to explain the principles of the invention. In the drawings wherein like reference numerals represent like parts:

FIG. 7 is a top view of the base shown in FIG. 1;

FIG. 10 is a bottom view of the tray shown in FIG. 1;

FIG. 11 is an enlarged, fragmentary, bottom view of the tray shown in FIG. 10;

FIG. 12 is an enlarged, fragmentary, bottom view of the tray shown in FIG. 11, the tray being shown with a projection on the base disposed within an associated opening in the tray, the projection being shown in cross-section;

DETAILED DESCRIPTION OF A PREFERRED EMBODIMENT

Figure 2:
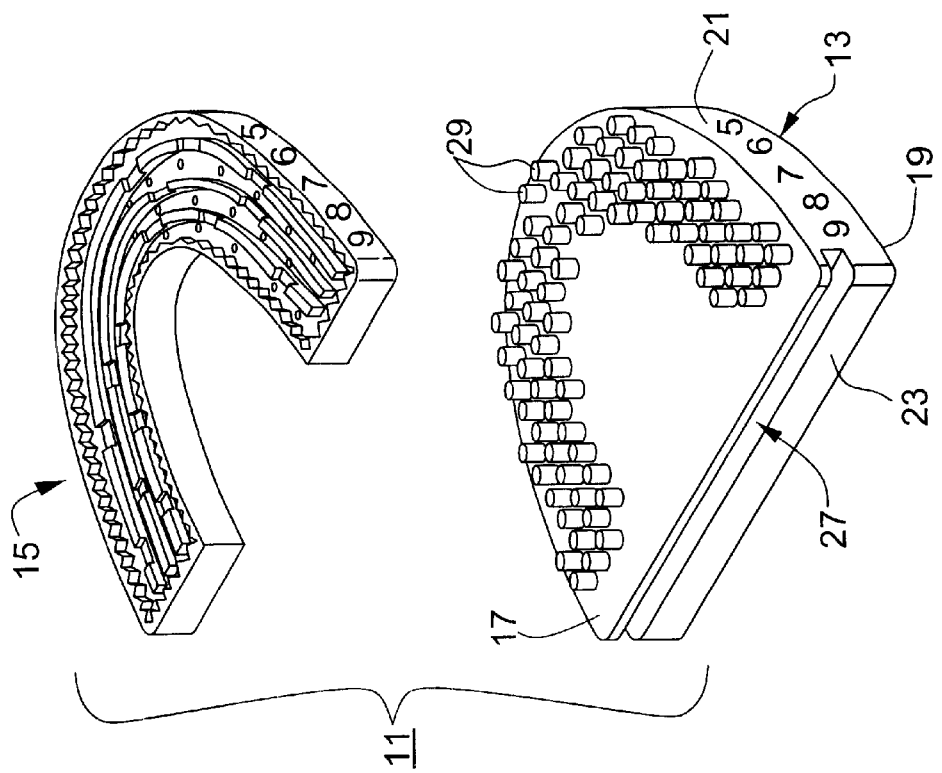
FIG. 2 is an exploded top perspective view of the dental cast tray assembly shown in FIG. 1.
Figure 1:
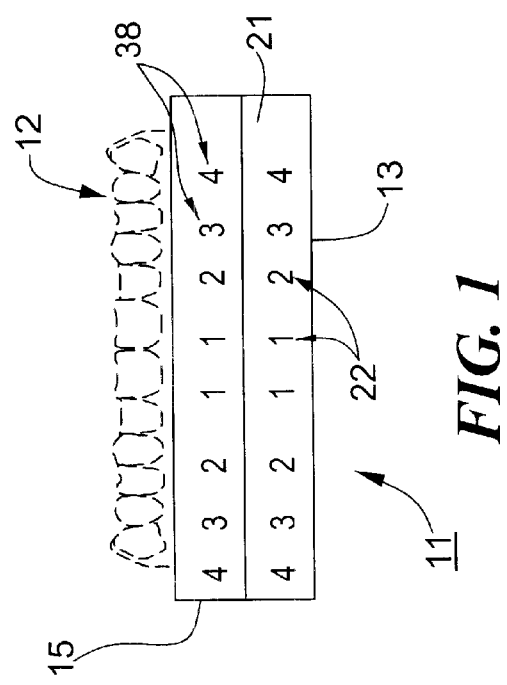
FIG. 1 is a front view of a first embodiment of a dental cast tray assembly constructed according to the teachings of the present invention, the dental cast tray assembly being shown with a positive dental cast model formed on the tray, the positive dental cast model being shown in phantom.

Referring now to FIGS. 1–2, there is shown a first embodiment of a dental cast tray assembly constructed according to the teachings of the present invention, the dental cast tray assembly being represented generally by reference numeral 11. As will be described further in detail below, dental cast tray assembly 11 can be used to form a dental cast model 12.

It should be noted that dental cast tray assembly 11 is shaped to approximate a full dental arch. As such, dental cast tray assembly 11 can be used to form a dental cast model 12 for either the upper jaw or the lower jaw of a patient. Accordingly, a pair of dental cast tray assemblies 11 can be supported by an articulator to create a positive dental cast model of the entire mouth of a patient which can then be used in the dental industry to manufacture crowns, bridges or other dental prosthetics.

It should be noted that dental cast tray assembly 11 is not limited to being shaped to approximate a full dental arch. Rather, it is to be understood that dental cast tray assembly 11 could be shaped to approximate less than a full dental arch without departing from the spirit of the present invention. As an example, dental cast tray assembly 11 could be shaped to approximate the left side, right side, or anterior quadrant of a full dental arch without departing from the spirit of the present invention. As another example, dental cast tray assembly 11 could be shaped to approximate a straight, or universal, quadrant of a full dental arch without departing from the spirit of the present invention, as will be described further in detail below.

Dental cast tray assembly 11 comprises a base 13 and a tray 15 removably mounted on base 13. Both base 13 and tray 15 are made of a plastic material which retains its rigidity in thin-wall construction and which is able to be easily manually cut by a saw blade. Preferably, base 13 is manufactured of an ABS plastic material and tray 15 is manufactured of a 20% glass-filled polycarbonate material.

Referring now to FIGS. 3–6, base 13 comprises a top surface 17, a bottom surface 19, an arcuate front wall 21 and a rear wall 23.

Bottom surface 19 is shaped to include a plurality of square-shaped recesses 25 in order to reduce the amount of plastic material required to manufacture base 13. It should be noted that bottom surface 19 is generally flat so as to enable base 13 to be placed on a working surface in a stable position.

Alignment indicia 22 are provided on arcuate front wall 21 of base 13. As will be described further in detail below, alignment indicia 22 provide a visible guide for ensuring proper alignment between tray 15 and base 13, as shown in FIG. 1. Preferably, alignment indicia 22 are in the form of sequential numbering. However, it is to be understood that any types of alignment indicia, such as alphabetical or symbolic designations, could be provided on front wall 21 of base 13 without departing from the spirit of the present invention.

Rear wall 23 is generally flat and is shaped to include an elongated recess 27. Elongated recess 27 is sized and shaped to receive a hinge for an articulator. As such, a pair of dental cast tray assemblies 11 can be supported by an articulator to create a positive dental cast model of the entire mouth of a patient, wherein an upper dental cast tray assembly is capable of centric, lateral and protrusive movement relative to a lower dental cast tray assembly.

It should be noted that elongated recess 27 is formed along the entire length of rear wall 23 to facilitate the installation of a hinge for an articulator therein. Specifically, the hinge of an articulator can easily be slid into elongated recess 27, from either side, to create a positive dental cast model for the entire mouth of a patient.

Figure 3:
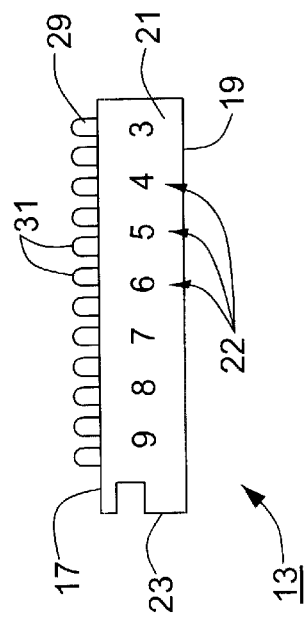
FIG. 3 is a top view of the base shown in FIG. 1.
Figure 5:
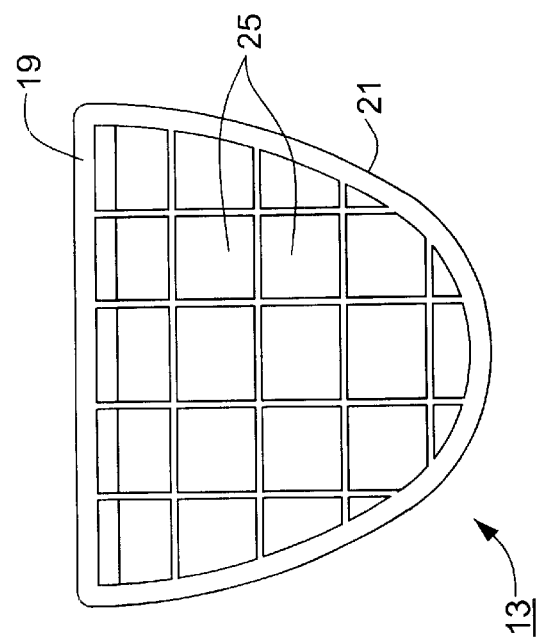
FIG. 5 is a bottom view of the base shown in FIG. 1.
Figure 4:
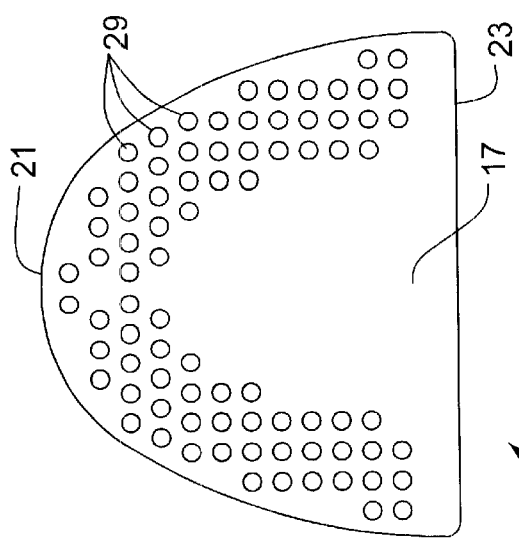
FIG. 4 is a rear view of the base shown in FIG. 1.
Figure 6:
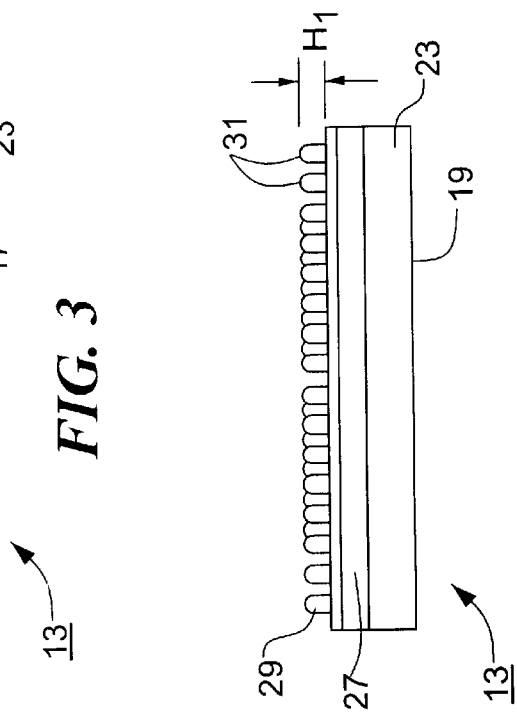
FIG. 6 is a side view of the base shown in FIG. 1.
Figure 8:
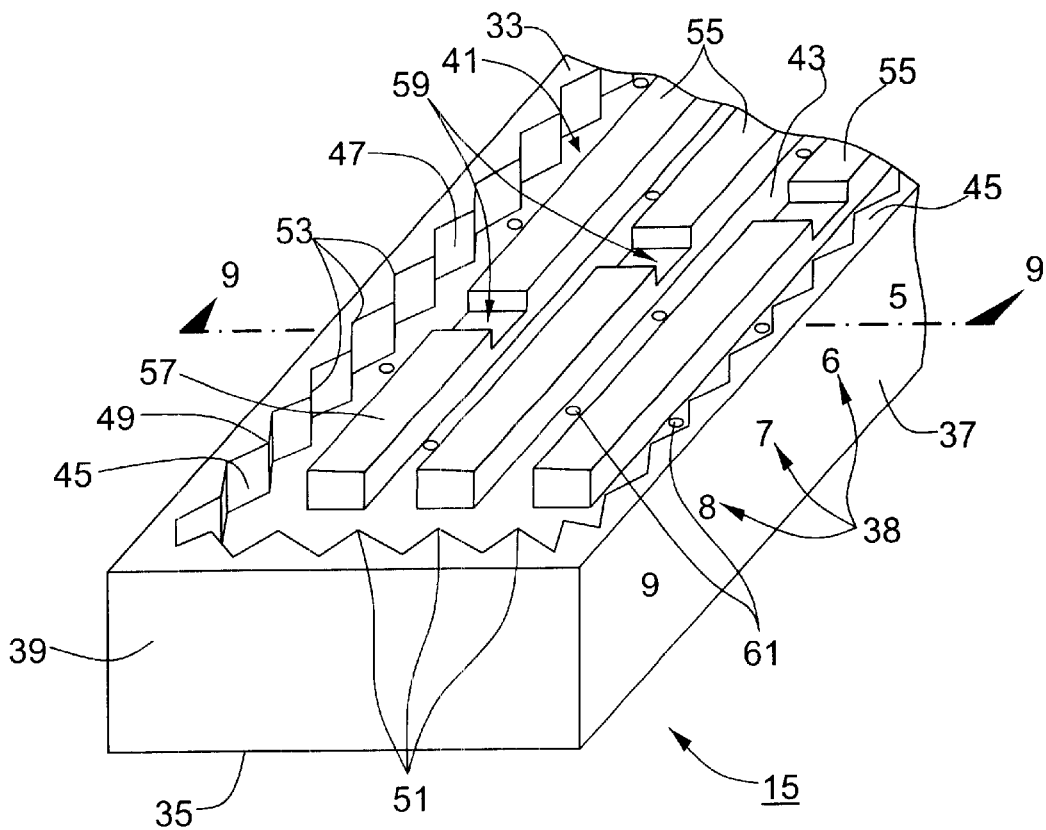
FIG. 8 is an enlarged, fragmentary, top perspective view of the tray shown in FIG. 1.
Figure 9:
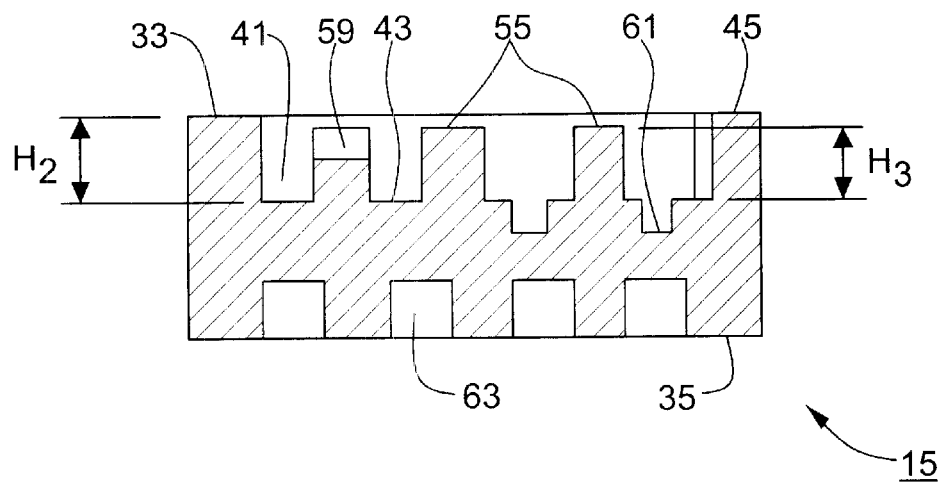
FIG. 9 is a section view, taken along lines 9—9, of the tray shown in FIG. 8.

Base 13 further comprises a plurality of generally cylindrically-shaped projections 29 which are formed on and protrude out from top surface 17. Each projection 29 has an approximate height $H_1$ of 5 mm and includes an outwardly curved free end 31. As shown in FIG. 3, projections 29 are patterned in a random order so as to ensure accurate alignment of tray 15 on base 13.

Referring now to FIGS. 7–12, tray 15 is a generally U-shaped, unitary member which is shaped to approximate a full dental arch. Tray 15 comprises a top surface 33, a generally flat bottom surface 35, an arcuate front wall 37 and a rear wall 39.

Top surface 33 of tray 15 is recessed so as to form an enclosed reservoir 41 for holding the casting material which is used to create dental cast model 12. Specifically, top surface 33 of tray 15 is recessed to form a substantially flat support surface 43 which is disposed between top surface 33 and bottom surface 35. Top surface 33 of tray 15 is recessed to also form a sidewall 45 which projects up from support surface 43 to top surface 33. Together, support surface 43 and sidewall 45 define enclosed reservoir 41.

It should be noted that sidewall 45 protrudes up from support surface 43 to top surface 33 along the entire outer periphery of support surface 43. In this manner, sidewall 45 serves as a wall for completely enclosing reservoir 41. As will be described further in detail below, entirely enclosing reservoir 41 serves to retain the casting material deposited therewithin during the dental model construction process, thereby preventing the casting material from spilling outside of reservoir 41 and onto front wall 37, rear wall 39 and base 13.

Sidewall 45 protrudes up from support surface 43 a height $H_2$ of approximately 3 mm and includes an inner surface 47. Inner surface 47 is shaped to include at least one surface irregularity 49 for retaining dental cast model 12 within reservoir 41. Specifically, inner surface 47 is shaped to include a plurality of V-shaped teeth 51 which protrude into reservoir 41. In addition, inner surface 47 is shaped to define a plurality of V-shaped grooves 53 therein. Together, teeth 51 and grooves 53 assist in the retention of dental cast model 12 within reservoir 41. It should be noted that inner surface 47 is not limited to the use of teeth 51 and grooves 53 to retain dental cast model 12 within reservoir 41. Rather, it is to be understood that alternative surface irregularities could be formed onto inner surface 47 without departing from the spirit of the present invention.

Alignment indicia 38 are provided on front wall 37 of tray 15. Alignment indicia 38 provide a visible guide for ensuring proper alignment between tray 15 and base 13 when tray 15 is mounted onto base 13. Specifically, as tray 15 is being mounted onto base 13, the user is able to visibly compare the position of indicia 38 on tray 15 relative to indicia 22 on base 13 in order to ensure that tray 15 is mounted on base 13 in proper alignment therewith, as shown in FIG. 1. Preferably, alignment indicia 38 are in the form of sequential numbering. However, it is to be understood that any types of matching alignment indicia, such as alphabetical or symbolic designation, could be provided on base 13 and tray 15 of dental cast tray assembly 11 without departing from the spirit of the present invention.

A plurality of elongated retention walls 55 are formed onto support surface 43 and project into reservoir 41, each retention wall 55 being generally rectangular in lateral cross-section. Retention walls 55 are disposed to extend along the length of reservoir 41 in a substantially parallel, spaced apart relationship. As will be described further in detail below, retention walls 55 assist in the retention of dental cast model 12 within reservoir 41.

It should be noted that tray 15 is not limited to the use of elongated, parallel, spaced apart, retention walls 55 to retain dental cast model 12 within reservoir 41. Rather, it is to be understood any suitable size, shape or number of projections could be formed on support surface 43 of tray 13 in order to retain dental cast model 12 within reservoir 41 without departing from the spirit of the present invention. For example, a plurality of cylindrical, rectangular or T-shaped posts could be formed on support surface 43 of tray 13 in place of retention walls 55 without departing from the spirit of the present invention.

Each retention wall 55 protrudes up from support surface 43 a height $H_3$ of approximately 2.8 mm. As such, the height $H_3$ in which each retention wall 55 protrudes up from support surface 43 is slightly less than the height $H_2$ in which each sidewall 45 protrudes up from support surface 43. Each retention wall 55 is shaped to include a substantially flat top surface 57 and a plurality of recesses 59 formed in top surface 57. Each recess 59 is generally rectangular in shape and extends down from top surface 57 approximately one-half the height $H_3$ of retention wall 55. Together, retention walls 55 and recesses 59 assist in the retention of dental cast model 12 within reservoir 41.

A plurality of retention openings 61 are formed into support surface 43. Retention openings 61 are formed so as to extend down from support surface 43 and towards bottom surface 35.

It should be noted that retention openings 61 are shown as cylindrically shaped holes. However, it is to be understood that retention openings 61 could be alternatively sized and shaped without departing from the spirit of the present invention. As an example, retention openings 61 could be in the form of one or more elongated channels, one or more rectangular holes or a combination thereof without departing from the spirit of the present invention.

Bottom surface 35 of tray 15 comprises a plurality of openings 63 which are patterned in the identical formation as projections 29 are patterned on base 13. As such, with tray 15 accurately mounted on base 13, one projection 29 will protrude into an associated opening 63, as shown in FIG. 12. It should be noted that accurate positive positional relationship is maintained between tray 15 and base 13 through the use of matching alignment indicia 22 and 38 and through the use of the interlocking and non-recurring geometric pattern of projections 29 on base 13 which matches the pattern of openings 63 on tray 15. Due to the irregular, non-repeating patterns, there is only one way or position in which tray 15 is mountable on base 13, openings 63 and projections 29 thereby acting an indexing function for proper alignment.

As shown in FIG. 11, each opening 63 formed in bottom surface 35 of tray 15 is generally square-shaped with rounded corners in lateral cross-section. As can be appreciated, the particular shape of each opening 63 enables an associated projection 29 to be easily inserted therein. Furthermore, the particular shape of each opening 63 serves to adequately retain an associated projection 29 therewithin with limited retention so as to create a snug, yet removable, fit, as shown in FIG. 12.

In use, dental cast tray assembly 11 can be used to manufacture dental cast model 12 in the following manner. Tray 15 is mounted on base 13 so that one projection 29 on base 13 protrudes into an associated opening 63 in tray 15. Preferably, tray 15 is firmly mounted onto base 13 in such a manner that substantially flat bottom surface 35 of tray 15 abuts against top surface 17 of base 13 in a plastic-to-plastic relation and so that arcuate front wall 37 of tray 15 is flush with arcuate front wall 21 of base 13, as shown in FIG. 1. An accurate positive positional relationship is maintained between tray 15 and base 13 through the use of matching alignment indicia 22 and 38 and through the use of the interlocking and non-recurring geometric pattern of projections 29 on base 13 and openings 63 on tray 15.

An impression tray filled with a rubber based material is used to take a negative impression of the upper or lower jaw of the mouth of a patient. If necessary, excess rubber based material is trimmed from the impression tray after the impression has been taken.

The negative impression is then transported to a dental laboratory where dental cast model 12 is manufactured. Specifically, a thick casting material, such as plaster, is deposited within the negative impression. At the same time, the thick plaster is deposited within the entire enclosed reservoir 41 of tray 15 using a laboratory utensil. It should be noted that the plaster is deposited into the entire reservoir 41 from support surface 43 to top surface 33. As such, the plaster fills retention openings 61, recesses 59 and grooves 53 and covers teeth 53 and retention walls 55.

It should be noted that, because reservoir 41 is entirely enclosed by sidewall 45, the thick plaster can be easily deposited and contained therewithin, which is highly desirable. As a result, dental cast tray assembly 11 is exceptionally easy to use and requires minimal clean-up, which is highly desirable.

With the plaster material deposited into the negative impression and into reservoir 41 of tray 15, the filled negative impression is then flipped over onto top surface 33 of tray 15 and is maintained in a stable position, thereby enabling the plaster in the negative impression and the plaster in reservoir 41 to mix together.

After the plaster material hardens approximately ½ hour later, the rubber impression is peeled off tray 15, thereby leaving positive plaster cast model 12. It should be noted that plaster cast model 12 is securely attached to tray 15 by the hardening of the mold material of model 12 onto retention walls 55 and inner surface 49 of side wall 45 and into retention openings 61 and recesses 59. Dental cast model 12 can then be used in the dental industry to manufacture crowns, bridges or other dental prosthetics.

Construction of a particular dental prosthetic begins by removing tray 15 from base 13. As can be appreciated, due to the limited retention of projections 29 within its associated openings 63, tray 15 can be easily removed from base 13. Removed from base 13, tray 15 is placed upon a flat cutting surface. Because bottom surface 35 of tray 15 is flat, tray 15 is stable when positioned upon the cutting surface.

With tray 15 positioned on the cutting surface, construction of the dental prosthetic requires isolation of the tooth or teeth for which the prosthesis will be constructed from the remaining teeth. This is accomplished by sawing down through dental cast model 12 and tray 15 on both sides of the teeth which will receive the prosthesis. Once the appropriate saw cuts have been made, the section of teeth which was isolated is removed to allow ease of manipulation during construction of the prosthesis.

Upon completion of the prosthesis, the isolated teeth, as well as the remaining untreated teeth, are remounted onto base 13 in the exact alignment prior to cutting, due to the irregular, non-repeating patterns of projections 29 and openings 63 as well as due to the use of matching alignment indicia 22 and 38. It should be noted that the convex shape of outwardly curved free end 31 of each projection 29 greatly facilitates the process of remounting tray 15 onto base 13. With tray 15 having been remounted on base 13, the dental technician is able to sufficiently inspect the precise relation of the prosthesis relative to the entire dental cast model 12.

As noted above, dental cast tray assembly 11 is not limited to being shaped to approximate a full dental arch. Rather, dental cast tray assembly 11 could be shaped to approximate less than a full dental arch without departing from the spirit of the present invention.

Figure 13:
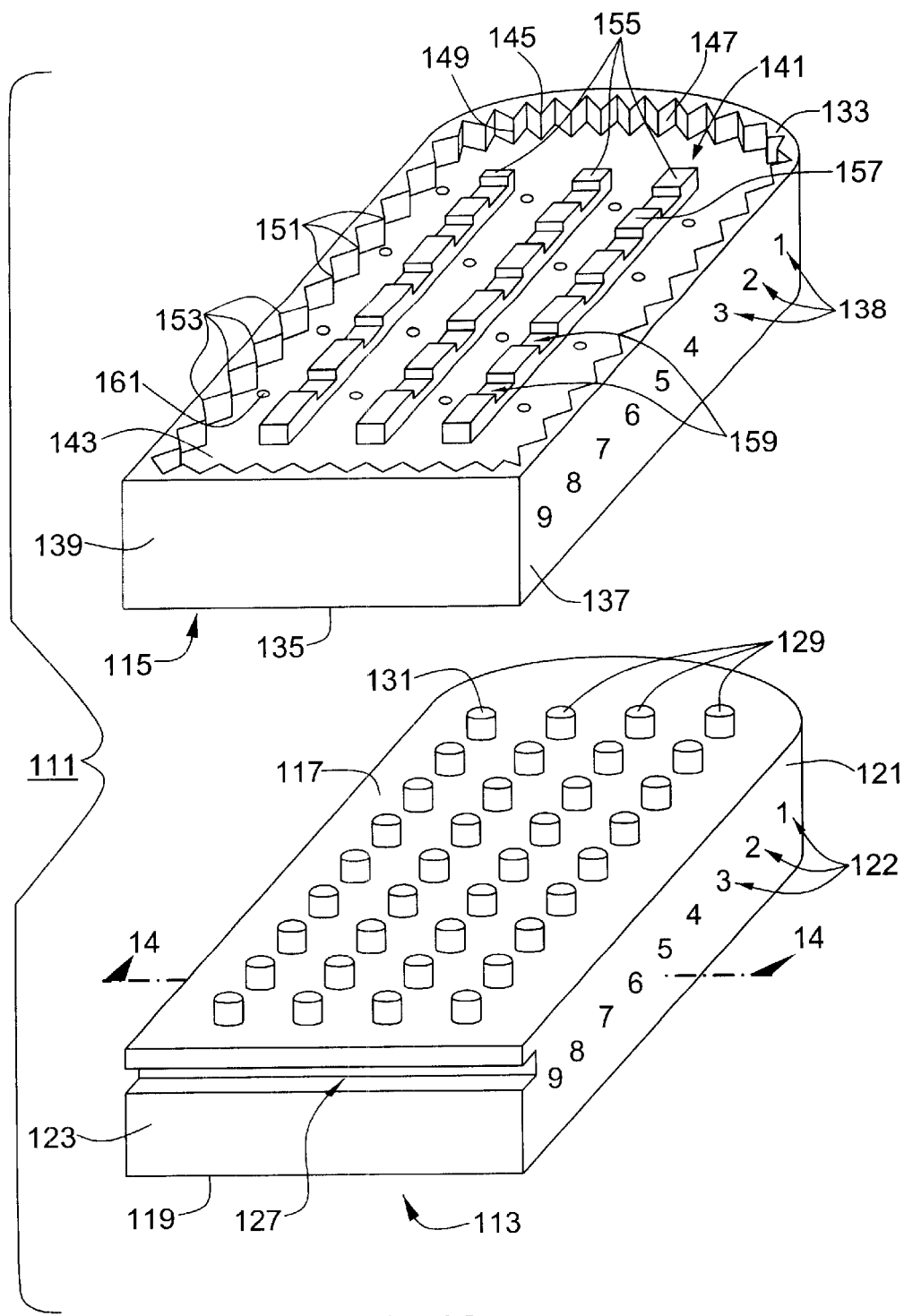
FIG. 13 is an exploded top perspective view of a second embodiment of a dental cast tray assembly constructed according to the teachings of the present invention.
Figure 14:
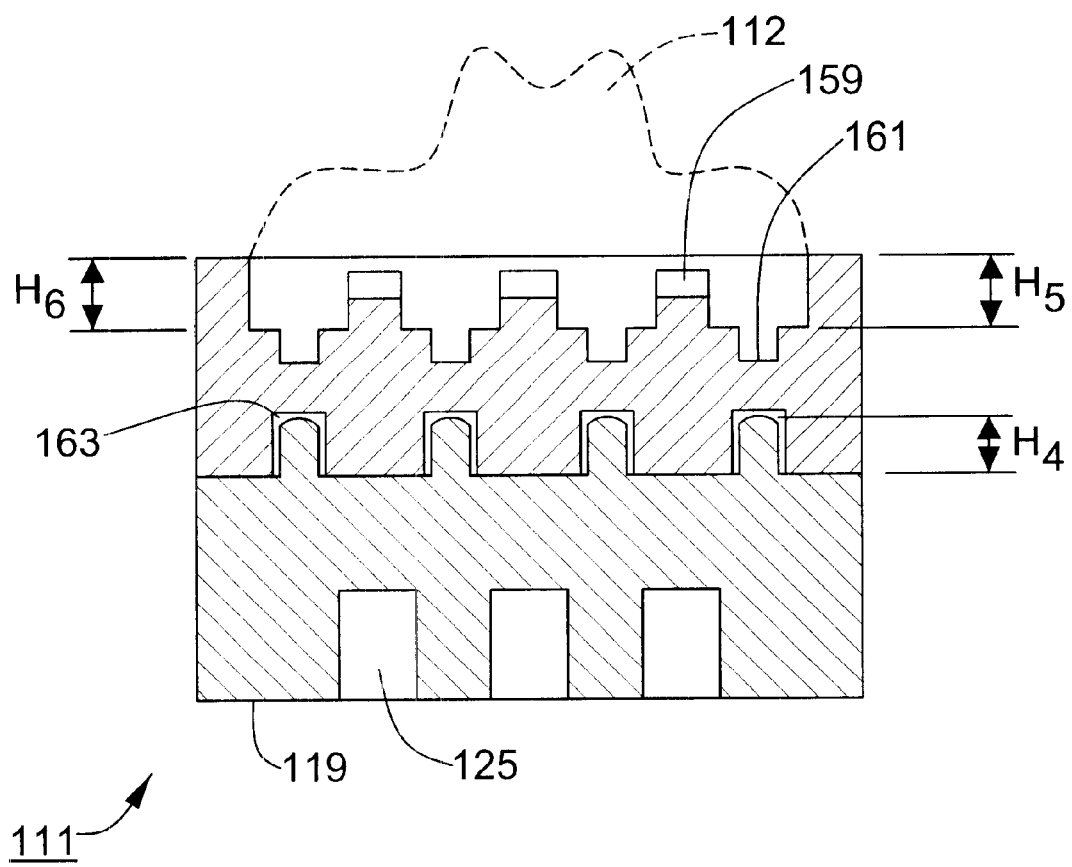
FIG. 14 is a section view, taken along lines 14—14, of the dental cast tray assembly shown in FIG. 13, the dental cast tray assembly being shown with the tray mounted on the base and with a positive dental cast model formed on the tray, the positive dental cast model being shown in phantom.

Accordingly, referring now to FIGS. 13 and 14, there is shown a second embodiment of a dental cast tray assembly constructed according to the teachings of the present invention, the dental cast tray assembly being represented generally by reference numeral 111.

Dental cast tray assembly 111 is similar to dental cast tray assembly 11 in that dental cast tray assembly 111 can be used to form a dental cast model 112.

The principal difference between dental cast tray assembly 111 and dental cast tray assembly 11 is that dental cast tray assembly 111 is shaped to approximate a straight, or universal, quadrant of a full dental arch, whereas dental cast tray assembly 11 is shaped to approximate a full dental arch. As can be appreciated, dental cast tray assembly 111 is preferred over dental cast tray assembly 11 when a dental cast model is required for a limited number of teeth, such as a single molar. Specifically, because dental cast tray assembly 111 utilizes less material to form dental cast model 112, use of dental cast tray assembly 111 over dental cast tray assembly 11 can provide cost savings, which is highly desirable.

Dental cast tray assembly 111 comprises a base 113 and a tray 115 removably mounted on base 113. Both base 113 and tray 115 are made of a plastic material which retains its rigidity in thin-wall construction and which is able to be easily manually cut by a saw blade. Preferably, base 113 is manufactured of an ABS plastic material and tray 115 is manufactured of a 20% glass-filled polycarbonate material.

Base 113 is a substantially straight member which comprises a top surface 117, a bottom surface 119, a generally U-shaped front wall 121 and a rear wall 123.

Bottom surface 119 is shaped to include a plurality of square-shaped recesses 125 in order to reduce the amount of plastic material required to manufacture base 113. It should be noted that bottom surface 119 is generally flat so as to enable base 113 to be placed on a working surface in a stable position.

Alignment indicia 122 are provided on front wall 121 of base 113. As will be described further in detail below, alignment indicia 122 provide a visible guide for ensuring proper alignment between tray 115 and base 113. Preferably, alignment indicia 122 are in the form of sequential numbering. However, it is to be understood that any types of alignment indicia, such as alphabetical or symbolic designations, could be provided on front wall 121 of base 113 without departing from the spirit of the present invention.

Rear wall 123 is generally flat and is shaped to include an elongated recess 127. Elongated recess 127 is sized and shaped to receive a hinge for an articulator. It should be noted that elongated recess 127 is formed along the entire length of rear wall 123 to facilitate the installation of a hinge for an articulator therein. Specifically, the hinge of an articulator can easily be slid into elongated recess 127 from either side of base 113.

Base 113 further comprises a plurality of generally cylindrically-shaped projections 129 which are formed on and protrude out from top surface 117. Each projection 129 has an approximate height $H_4$ of 5 mm and includes an outwardly curved free end 131. Projections 129 are arranged on top surface 117 in a patterned configuration. However, it is to be understood that projections 129 could be alternatively configured in a random order so as to ensure accurate alignment of tray 115 on base 113 without departing from the spirit of the present invention.

Tray 115 is substantially straight member which comprises a top surface 133, a generally flat bottom surface 135, a generally U-shaped front wall 137 and a rear wall 139.

Top surface 133 of tray 115 is recessed so as to form an enclosed reservoir 141 for holding the casting material which is used to create dental cast model 112. Specifically, top surface 133 of tray 115 is recessed to form a substantially flat support surface 143 which is disposed between top surface 133 and bottom surface 135. Top surface 133 of tray 115 is recessed to also form a sidewall 145 which projects up from support surface 143 to top surface 133. Together, support surface 143 and sidewall 145 define enclosed reservoir 141.

It should be noted that sidewall 145 protrudes up from support surface 143 to top surface 133 along the entire outer periphery of support surface 143. In this manner, sidewall 145 serves as a wall for completely enclosing reservoir 141. As can be appreciated, entirely enclosing reservoir 141 serves to retain the casting material deposited therewithin during the dental model construction process, thereby preventing the casting material from spilling outside of reservoir 141 and onto front wall 137, rear wall 139 and base 113.

Sidewall 145 protrudes up from support surface 143 a height $H_5$ of approximately 3 mm and includes an inner surface 147. Inner surface 147 is shaped to include at least one surface irregularity 149 for retaining dental cast model 112 within reservoir 141. Specifically, inner surface 147 is shaped to include a plurality of V-shaped teeth 151 which protrude into reservoir 141. In addition, inner surface 147 is shaped to define a plurality of V-shaped grooves 153 therein. Together, teeth 151 and grooves 153 assist in the retention of dental cast model 112 within reservoir 141. It should be noted that inner surface 147 is not limited to the use of teeth 151 and grooves 153 to retain dental cast model 112 within reservoir 141. Rather, it is to be understood that alternative surface irregularities could be formed onto inner surface 147 without departing from the spirit of the present invention.

Alignment indicia 138 are provided on front wall 137 of tray 115. Alignment indicia 138 provide a visible guide for ensuring proper alignment between tray 115 and base 113 when tray 115 is mounted onto base 113. Specifically, as tray 115 is being mounted onto base 113, the user is able to visibly compare the position of indicia 138 on tray 115 relative to indicia 122 on base 113 in order to ensure that tray 115 is mounted on base 113 in proper alignment therewith. Preferably, alignment indicia 138 are in the form of sequential numbering. However, it is to be understood that any types of matching alignment indicia, such as alphabetical or symbolic designation, could be provided on base 113 and tray 115 of dental cast tray assembly 111 without departing from the spirit of the present invention.

A plurality of elongated retention walls 155 are formed onto support surface 143 and project into reservoir 141, each retention wall 155 being generally rectangular in lateral cross-section. Retention walls 155 are disposed to extend along the length of reservoir 141 in a substantially parallel, spaced apart relationship. As can be appreciated, retention walls 155 assist in the retention of dental cast model 112 within reservoir 141.

It should be noted that tray 115 is not limited to the use of elongated, parallel, spaced apart, retention walls 155 to retain dental cast model 112 within reservoir 141. Rather, it is to be understood any suitable size, shape or number of projections could be formed on support wall 143 of tray 113 in order to retain dental cast model 112 within reservoir 141 without departing from the spirit of the present invention. For example, a plurality of cylindrical, rectangular or X-shaped posts in lateral cross-section could be formed on support surface 143 of tray 113 in place of retention walls 155 without departing from the spirit of the present invention.

Each retention wall 155 protrudes up from support wall 143 a height $H_6$ of approximately 2.8 mm. As such, the height $H_6$ in which each retention wall 55 protrudes up from support wall 43 is slightly less than the height $H_5$ in which each sidewall 45 protrudes up from support wall 43.

Each retention wall 155 is shaped to include a substantially flat top surface 157 and a plurality of recesses 159 formed in top surface 157. Each recess 159 is generally rectangular in shape and extends down from top surface 157 approximately one-half the height $H_6$ of retention wall 155. Together, retention walls 155 and recesses 159 assist in the retention of dental cast model 112 within reservoir 141.

A plurality of retention openings 161 are formed into support surface 143. Retention openings 161 are formed so as to extend down from support surface 143 and towards bottom surface 135.

It should be noted that retention openings 161 are shown as cylindrically shaped holes. However, it is to be understood that retention openings 161 could be alternatively sized and shaped without departing from the spirit of the present invention. As an example, retention openings 161 could be in the form of one or more elongated channels, one or more rectangular holes or a combination thereof without departing from the spirit of the present invention.

Bottom surface 135 of tray 115 comprises a plurality of openings 163 which are patterned in the identical formation as projections 129 are patterned on base 113. As such, with tray 115 accurately mounted on base 113, one projection 129 will protrude into an associated opening 163, as shown in FIG. 14.

Each opening 163 formed in bottom surface 135 of tray 115 is generally square-shaped with rounded corners in lateral cross-section. As can be appreciated, the particular shape of each opening 163 enables an associated projection 129 to be easily inserted therein. Furthermore, the particular shape of each opening 163 serves to adequately retain an associated projection 129 therewithin with limited retention so as to create a snug, yet removable, fit, as shown in FIG. 14.

The embodiment of the present invention described above is intended to be merely exemplary and those skilled in the art shall be able to make numerous variations and modifications to it without departing from the spirit of the present invention. All such variations and modifications are intended to be within the scope of the present invention as defined in the appended claims.

What is claimed is:

1. A dental cast tray assembly for forming a dental cast model, comprising:
   (a) a base; and
   (b) a tray removably mounted on said base, said tray comprising a bottom surface and a top surface, the top surface being recessed so as to form a support surface and a sidewall which protrudes up from the support surface to the top surface along its entire length, the sidewall and the support surface together defining an enclosed reservoir for holding the dental cast model.

2. The dental cast tray assembly of claim 1 wherein the sidewall protrudes up from the support surface of said tray a height of approximately 3 mm.

3. The dental cast tray assembly of claim 1 wherein the sidewall of said tray includes an inner surface and an outer surface, the inner surface of the sidewall being shaped to include at least one surface irregularity for retaining the dental cast model within the enclosed reservoir.

4. The dental cast tray assembly of claim 3 wherein the at least one surface irregularity is in the form of a tooth which protrudes out from the inner surface of the sidewall and into the reservoir.

5. The dental cast tray assembly of claim 4 wherein the tooth is generally V-shaped.

6. The dental cast tray assembly of claim 3 wherein the at least one surface irregularity is in the form of a groove formed into the inner surface of the sidewall.

7. The dental cast tray assembly of claim 6 wherein the groove is generally V-shaped.

8. The dental cast tray assembly of claim 1 wherein the sidewall of said tray includes an inner surface and an outer surface, the inner surface of the sidewall being shaped to include a plurality of teeth which protrude into the reservoir, the inner surface of the sidewall being shaped to define a plurality of grooves formed therein.

9. The dental cast tray assembly of claim 1 wherein said tray comprises a projection disposed within the reservoir of said tray for retaining the dental cast model.

10. The dental cast tray assembly of claim 1 wherein said tray comprises a projection formed on the support surface of said tray for retaining the dental cast model.

11. The dental cast tray assembly of claim 10 wherein the projection protrudes up from the support surface of said tray a height of approximately 2.8 mm.

12. The dental cast tray assembly of claim 10 wherein said projection is in the form of a retention wall having a top platform.

13. The dental cast tray assembly of claim 12 wherein the top platform of the retention wall includes at least one recess formed therein for retaining the dental cast model.

14. The dental cast tray assembly of claim 13 wherein the height in which the retention wall protrudes up from the support surface of said tray is less than the height in which the sidewall protrudes up from the support surface of said tray.

15. The dental cast tray assembly of claim 13 wherein the at least one recess extends partially down from the top platform of the retention wall.

16. The dental cast tray assembly of claim 1 wherein the support surface of said tray is shaped to include at least one retention hole for holding the dental cast model.

17. The dental cast tray assembly of claim 1 wherein said tray is shaped to approximate a straight quadrant.

18. The dental cast tray assembly of claim 1 wherein said base comprises a generally flat top surface, a bottom surface and a plurality of projections formed on the top surface.

19. The dental cast tray assembly of claim 18 wherein the bottom surface of said tray is generally flat and is shaped to include a plurality of openings formed therein, each of the plurality of openings being sized and shaped to receive an associated projection when said tray is mounted on said base, the bottom surface of said tray abutting against the top surface of said base when said tray is mounted on said base.

20. A dental cast tray assembly for forming a dental cast model, comprising:
   (a) a base; and
   (b) a tray removably mounted on said base, said tray comprising a bottom surface and a top surface, the top surface being recessed so as to form a support surface and a fixed sidewall which protrudes up from the support surface, said sidewall formed along the entire periphery of the support surface, the sidewall and the support surface together defining an enclosed reservoir for holding the dental cast model.

* * * * *